United States Patent [19]
Haerten

[11] 4,346,717
[45] Aug. 31, 1982

[54] DEVICE FOR PUNCTUATING INTERNAL BODY ORGANS, VESSELS OR THE LIKE

[75] Inventor: Rainer Haerten, Roettenbach, Fed. Rep. of Germany

[73] Assignee: Siemens Aktiengesellschaft, Berlin & Munich, Fed. Rep. of Germany

[21] Appl. No.: 179,082

[22] Filed: Aug. 18, 1980

[30] Foreign Application Priority Data

Sep. 7, 1979 [DE] Fed. Rep. of Germany ....... 2936259

[51] Int. Cl.³ .............................................. A61B 10/00
[52] U.S. Cl. .................................................... 128/660
[58] Field of Search ................... 128/660–663, 128/24 A, 653, 657, 754; 73/597, 618–626; 340/720, 723–724, 732, 736, 739, 744

[56] References Cited

U.S. PATENT DOCUMENTS

| | | | |
|---|---|---|---|
| 3,556,079 | 6/1971 | Omiyo | 128/24 A |
| 3,721,227 | 3/1973 | Larson et al. | 128/24 A |
| 4,029,084 | 6/1977 | Soldner | 128/660 |
| 4,058,114 | 11/1977 | Soldner | 128/660 |
| 4,108,165 | 8/1978 | Kopp et al. | 128/660 |
| 4,141,347 | 2/1979 | Green et al. | 128/663 |
| 4,154,114 | 5/1979 | Katy et al. | 128/660 X |
| 4,209,022 | 6/1980 | Dory | 128/660 |
| 4,249,539 | 2/1981 | Vilkomerson et al. | 128/660 |
| 4,259,725 | 3/1981 | Andrews et al. | 340/724 X |

FOREIGN PATENT DOCUMENTS

| | | | |
|---|---|---|---|
| 2148700 | 10/1976 | Fed. Rep. of Germany | 128/660 |
| 2619723 | 11/1976 | Fed. Rep. of Germany | 128/660 |
| 2906474 | 8/1979 | Fed. Rep. of Germany | 128/660 |
| 7513862 | 11/1975 | Netherlands | 128/660 |

OTHER PUBLICATIONS

Kendall, P. H., "A Trephine Needle for Vertebral Body Biopsy", Lancet, Feb. 27, 1960, p. 35.
American Journal of Obstetrics & Gynecology, vol. 114, No. 5, Nov. 1, 1972, (US) J. Bang et al., "A New Ultrasonic Method for Transabdominal Amniocentesis", pp. 599–601.
Electromedica (Siemens), vol. 42, No. 3, 1974 Erlangen (DE) W. Jonatha: "Amniozentese in der Frühschwangerschaft unter Sicht kontrolle mit Ultraschall", pp. 94–96.
Ultrasonics, vol. 10, No. 2, März 1972 Guildford (GB)/ H. H. Holm et al: "Ultrasound as a guide in percutaneous puncture technique", pp. 83–86.

Primary Examiner—Kyle L. Howell
Assistant Examiner—Francis J. Jaworski
Attorney, Agent, or Firm—Hill, Van Santen, Steadman, Chiara & Simpson

[57] ABSTRACT

The circuitry comprises directing circuits for producing, and superimposing on an image of a body displayed by such display equipment, a guide image beam; the position of which guide image beam can be adjusted to lie in a desired direction with respect to such a body image in order to provide information to facilitate operation of such a puncturing device, to puncture the body substantially in the said desired direction.

29 Claims, 4 Drawing Figures

DEVICE FOR PUNCTUATING INTERNAL BODY ORGANS, VESSELS OR THE LIKE

BACKGROUND OF THE INVENTION

This invention relates to circuitry adapted for use with image display equipment of ultrasonic scanning apparatus to facilitate puncturing of a body by a puncturing device associated with such scanning apparatus.

In the prior art a whole series of equipment is already known which is intended to facilitate piercing by a puncturing cannula of an organ or vessel aimed at in an arcuate manner with fine needle puncturing. The majority function with the aid of ultrasound. Thus, for example, U.S. Pat. No. 3,721,227 discloses a sound head with a central bore hole which acts as a guiding aid for a puncturing cannula. However, this puncturing device does not allow any puncture control in the real time echo image. On the contrary, provision is made for such control in the case of an ultrasonic applicator having a central, oblique slit location as is described, for example, in U.S. Pat. No. 4,029,084. However, the guiding bore opens into the row of ultrasonic transducer elements; since at least the central transducer element must be recessed, this can result in losses of sensitivity in the center. A further possibility for aiding puncturing is disclosed in U.S. Pat. No. 3,556,079, or even in German Patent No. 21 48 700. However, here, puncturing is limited to vessels or organs having blood flowing through them so that the ultrasonic Doppler technique is used as an aid without sectional image synthesis. Therefore, in these cases, the piercing process is closed to observation in the real-time image. A further puncturing possibility is known from the Lancet journal dated Feb. 21, 1960, page 35. Here, a scale is placed on the surface of the body within which an organ, vessel or the like is to be punctured by way of control in an x-ray image, the scale having, at one end, an aid for guiding a puncturing cannula which is inclined at a certain angle. The piercing direction can then be determined by displacing the scale at the intervals which can be taken from the display image with a prescribed angle.

U.S. Pat. No. 4,058,114 describes puncturing apparatus which comprises a guiding aid for a puncturing cannula, which is arranged to the side of an ultrasonic applicator. Also, there is mounted on a display unit, likewise to the side, a mechanical target pin which is adjustable for aiming at a puncturing area in the echo sectional image on the image screen of the display unit. The target angle of the target pin can be transferred as a piercing angle as an aid for introducing the puncturing cannula. The entire arrangement has the particular advantage that, using real-time control in the ultrasonic echo sectional image, it is also possible for piercing to take place to the side of the actual bearing surface of the ultrasonic applicator. Less advantageous, however, is the fact that a corresponding mechanical assembly is also required as a target aid on the display unit itself; this is relatively bulky and, moreover, in terms of adjustment, is time-consuming and complicated.

SUMMARY OF THE INVENTION

According to the invention there is provided ultrasound imaging apparatus including circuitry associated with image display equipment, and ultrasound signal applicator means with guiding means and angle detecting means to facilitate puncturing of a body by a puncturing device associated with such guiding means, the circuitry comprising directing circuit means for producing, and superimposing on an image of a body displayed by such display equipment, a guide image beam; the position of which guide image beam can be adjusted to lie in a desired direction with respect to such a body image in order to provide information to facilitate operation of such a puncturing device, to puncture the body substantially in the said desired direction. This guiding means could comprise angle detecting means for detecting the angle of the puncturing device with respect to a body being treated in use, and for supplying a signal to the directing means for adjusting the position of the guide image.

Alternatively, the directing means could be adapted such that, in use, the guide image is maintained at a fixed position with respect to the body image, corresponding to a fixed position of the guiding means and hence the puncturing device with respect to such ultrasound signal applicator means, puncturing of the body in substantially the desired direction being achieved by displacement of the applicator means with respect to the body.

The directing means could comprise a calculator for producing an intensity modulating signal during the display of the relevant segment of the image field for supply to such image display equipment for producing the guide image beam. In this case, the intensity modulating signal is preferably produced in use as a function of signals from a horizontal time base generator and a vertical time base generator of such image display equipment, and as a function of a signal from the angle detecting means. The intensity modulating signal could comprise a series of pulses. In this case, the series of pulses could produce the beam by producing a corresponding series of intensity-modulated spots on an image displayed by such image display equipment in use. Preferably the pulses are produced at the line synchronization frequency of time base pulses from the horizontal time base generator. Alternatively, the pulses could be produced at regular intervals such that the intensity-modulated spots are produced at regular intervals along the beam such that the beam is in the form of a scale.

Such an intensity modulating signal is preferably produced in use according to the relationship:

$$t(X) = X/v \cdot \tan \theta;$$

where $X = x + k;$
and where: t is the course of horizontal time base pulses from the horizontal time base generator; X is the course of vertical time base pulses from the vertical time base generator; v is the sweep speed of ultrasonic waves in the body being treated; $\theta$ is an angle detected by the angle detecting means; x is an image coordinate of a target area of the body to be punctured by such a puncturing device; and k is the distance from a point of intersection of the puncturing device with a reference plane for the guide image to the image coordinate origin. In this case, a further calculator is preferably provided, associated with the first-mentioned calculator, for producing output pulses at time intervals $\tau$, where:

$$\tau = a \cos \theta / v;$$

where a is a predetermined increment for the scale. The predetermined increment is preferably approximately 5 mm. Also, the circuitry preferably further comprises an AND gate, first and second inputs of which are connectable with outputs of the first and second mentioned calculators respectively such that, in use, in order to produce a beam in the form of a scale, pulses are supplied by an output of the AND gate to intensity modulating circuitry of such image display equipment only when an intensity modulating signal produced by the first-mentioned calculator coincides with an output pulse from the second-mentioned calculator.

The circuitry could be provided with means for superimposing, on an image of a body displayed by such display equipment, a measuring image which can be displaced with respect to the body image to a target area in the body image, and means for measuring the displacement of the measuring image from a reference point on the surface of the body to the target area. This measuring image could be displaced, in use, along the beam, when the guide image is in the form of a beam. Also, means could be provided for digitally indicating the measured displacement of the measuring image. Furthermore, means could be provided for automatically superimposing, on the body image at the said reference point, a further measuring image for indicating the point on the body surface at which the puncturing device should enter the body. The reference point is preferably located on the said reference plane.

The guiding means of the ultrasound signal applicator means could also be provided with a puncturing device, preferably a cannula. In this case, the guiding means, when present, preferably comprises a guide sleeve for a needle associated with the cannula, the guide sleeve being detachably mounted on the guiding means such that, in use, after puncturing of a body, the applicator means can be detached from the cannula and removed.

The invention will now be described, by way of example, with reference to the accompanying drawings; and other objects, features and advantages will be apparent from this detailed disclosure and from the appended claims.

BRIEF DESCRIPTION OF THE DRAWINGS

FIG. 1 shows a side view and FIG. 1A shows an end view of part of one type of ultrasonic scanning apparatus (comprising an ultrasonic array) and part of a body;

DETAILED DESCRIPTION

Figure 1:
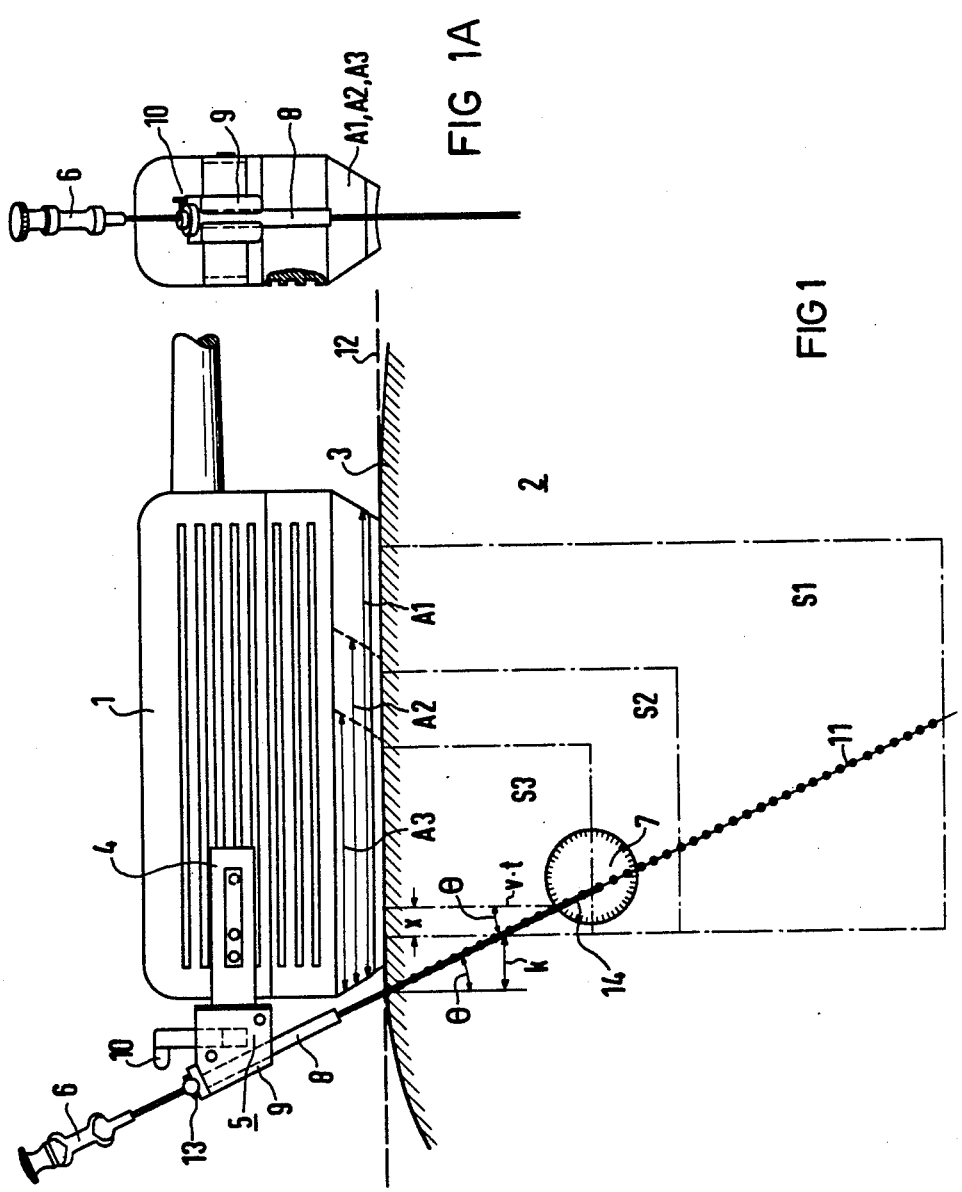

Referring to FIG. 1, an ultrasonic applicator in the form of an ultrasonic array 1 has an active element face A1. A sectional image S1 can be produced inside an examination subject 2 with the array 1 placed on a body surface 3 of the subject 2. If a puncturing device is used in conjunction with further arrays having active element faces A2 and A3 (giving sectional images S2 and S3 respectively) and, for example, varying ultrasonic frequency, then a common switching arrangement can be used if these faces A1, A2, and A3 are designed in such a way that the side edges of the sectional images S1, S2, S3 coincide with the side of puncturing devices of various sizes. Therefore, in the embodiment of FIG. 1, a guiding aid 5 for introducing a puncturing cannula 6 into a target area 7 in the examination subject 2 is arranged on the left-hand side on the array 1 by means of mounting brackets 4. The guiding aid 5 comprises, in detail, a guide sleeve 8, for the puncturing cannula 6, and a clamp 9 secured to the mounting brackets 4 for holding the guide sleeve 8. The clamp 9 is provided with an opening lever 10; when this lever 10 is actuated, the clamp 9 can be opened and the cannula 6, together with the guide sleeve 8, can be removed from the clamp 9. Therefore, when the cannula 6 has pierced the examination subject 2, by opening the clamp 9 the entire ultrasonic array 1 can be detached from the cannula 6 if required. When the array 1 is detached, the actual biopsy can be carried out unhindered.

The sectional images S1, S2 and S3 shown in FIG. 1 can be represented in a known manner as echo sectional images on a display screen of a cathode ray tube (not shown). As is shown in FIG. 1, a guide image in the form of a guide beam 11 is electronically superimposed also on this display screen. The guide beam 11 is shown on the display screen as a multiplicity of bright, intensity modulated (unblanking) points arranged along a straight line.

The intensity modulated points of the guide beam 11 can follow on from one another at fixed, preset intervals, for example at 5 mm intervals, so that, in addition to providing a target aid for the cannula 6, the guide beam 11 provides, at the same time, an electronic measurement scale from which it is possible to read the depth of the object to be punctured, in this example the target area 7, from the body surface 3 on which the array 1 lies, immediately and without any problems. In FIG. 1 the electronic guide beam 11 is shown disposed at an angle $\theta$ with respect to the beam direction of ultrasonic beams (not shown) emitted by the ultrasonic array 1, which angle $\theta$ corresponds to the angle of the piercing direction for the cannula 6 into the examination subject 2.

The coordinating of the angle $\theta$ representing a piercing direction of the cannula 6 and the direction of the guide beam 11 could be arranged such that positioning signals are derived for the guide beam 11 in the echo sectional image as a function of an angle-adjusting element (not shown) provided on the guiding aid 5 of the cannula 6. By swivelling the guide sleeve (needle guide) 8 for the cannula 6, the guide beam 11 could also be swivelled by means of such positioning signals until it arrives at the target area 7 aimed at. The cannula 6 would then be aimed directly at this target area 7.

In the case of the array 1 shown in FIG. 1, however, a much simpler arrangement is used. Here, the guide sleeve 8 for the cannula 6 is arranged at a fixed angle $\theta$ of, for example, 20° with respect to the ultrasonic array 1. The guide beam 11 is superimposed on the display screen of the cathode ray tube likewise at this fixed angle $\theta$. Lateral displacement k, which arises due to the lateral arrangement of the guiding aid 5 on the array 1, is automatically taken into account for the guide beam 11 when the latter is superimposed on the display screen. Thus, the direction and spacial position of the guide beam 11 on the display screen always automatically corresponds to the piercing direction and target position of the cannula 6 with respect to the array 1. The target area 7 to be punctured is aimed at simply by spacial displacement of the ultrasonic array 1 on the body surface 3 until the guide beam 11 superimposed on the displayed image passes through the target area 7 to be punctured. The cannula 6 is then directly aligned with the target area 7 to be punctured so that piercing can commence. The piercing process itself takes place preferably under ultrasonic image control, with or without the use of a scale. It can also be carried out blind, whereby, however, a depth carrier 13 must be used, at least in the latter case. Such a depth carrier is described, for example, in German Patent No. 21 48 700. After concluding the piercing process, i.e. when the point of the cannula 6 has reached the target area 7 of the biopsy, it is possible to actually remove tissue or tissue fluid from the examination subject 2 for examination purposes. As already mentioned above, the array 1 can be detached from the cannula 6 for this purpose.

The application of the guide beam principle described with reference to FIG. 1 is completely independent of the type of design of the ultrasonic applicator used. In place of an ultrasonic array 1, an applicator which is constructed in any other manner, for example one with a transducer for rotating in the focal point of a parabolic reflector, or one for sector scanning, as is shown in FIG. 2, can also be used.

Figure 2:
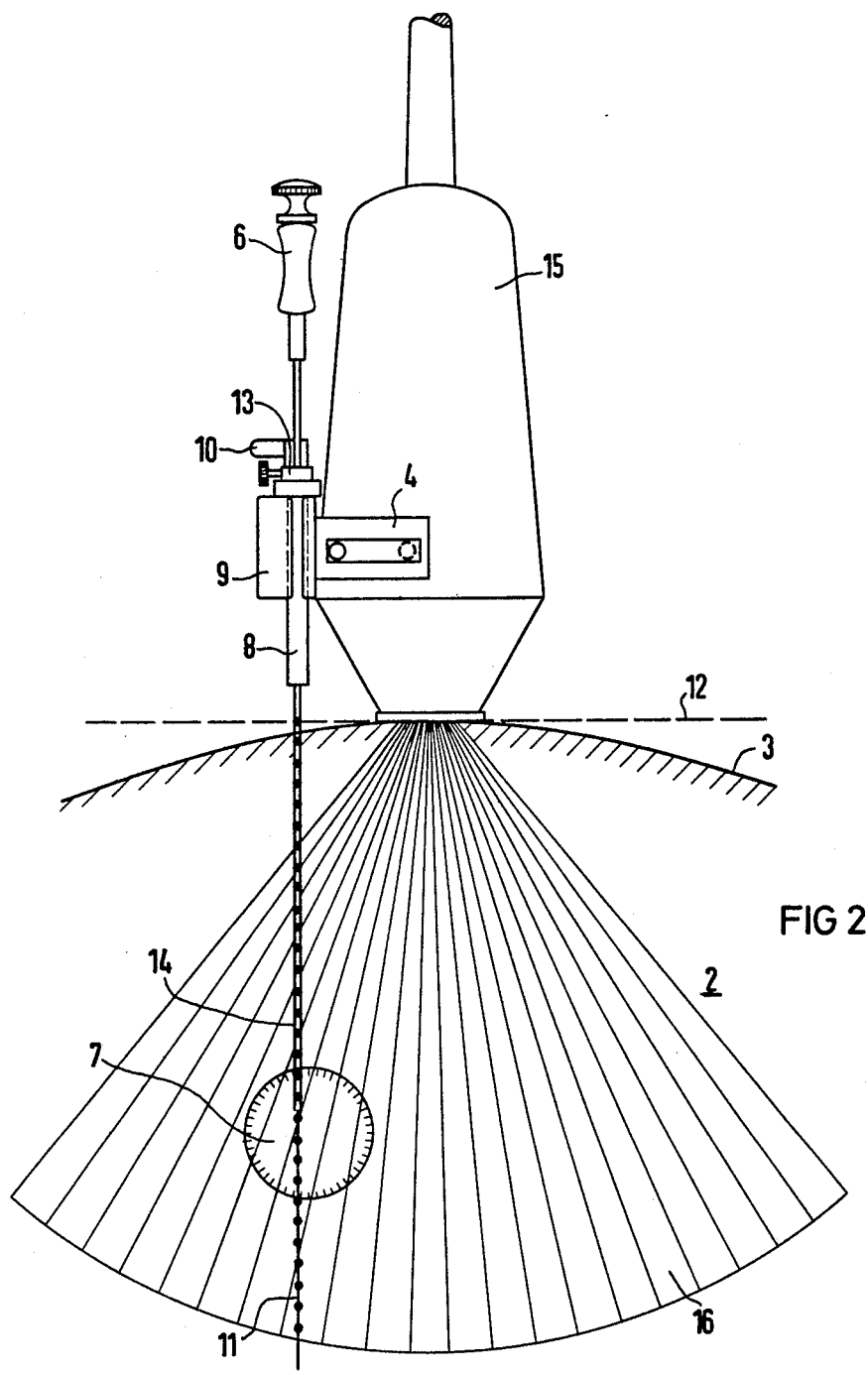
FIG. 2 shows a side view of part of a second type of ultrasonic scanning apparatus (comprising a sector scanner) and part of a body.

Referring to FIG. 2, a sector scanner is denoted by the reference numeral 15 and a sector scanning field which it produces in use is denoted by the reference numeral 16. In contrast to the embodiment shown in FIG. 1, here, the guide sleeve 8, for the puncturing cannula 6, is also arranged on the sector scanner 15 in such a manner that a piercing angle of zero degrees ($\theta = 0°$) is produced for the guide beam 11 with respect to the normal to a reference plane 12. Accordingly, the guide beam 11 then also extends in the direction of the normal; that is, it is perpendicular to the reference plane 12.

Figure 3:
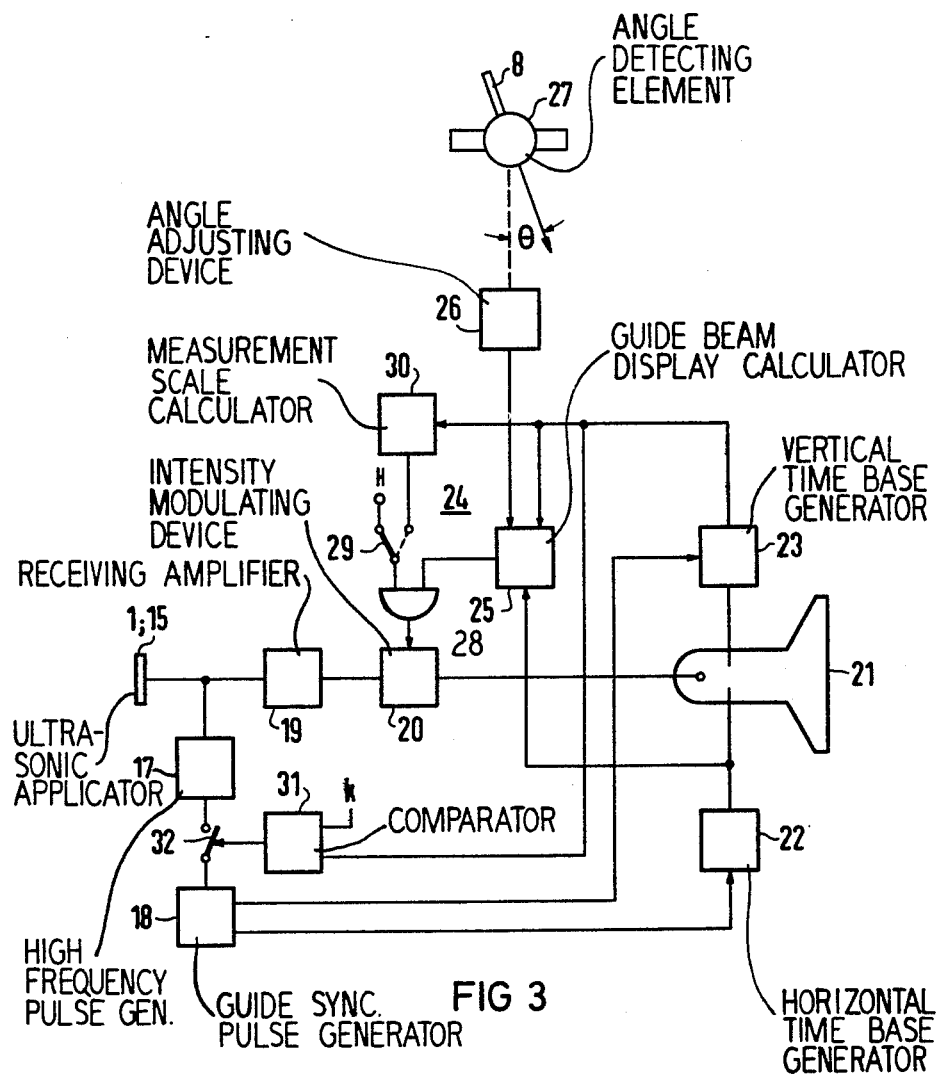
FIG. 3 shows a block circuit diagram of an arrangement incorporating circuitry according to the invention for use with the scanning apparatus shown in FIGS. 1 and 2.

A block circuit diagram of an arrangement for producing an echo sectional image with a superimposed guide beam is shown in FIG. 3. The ultrasonic applicator in the circuit diagram corresponds either to the array 1 of FIG. 1 or to the sector scanner 15 of FIG. 2, or it could be constructed in any other form. High frequency pulses produced by a high frequency generator 17 are fed to ultrasonic transducers (not shown) of the applicator 1; 15 in synchronism with guide pulses produced by a guide sync pulse generator 18 for the purpose of emitting ultrasonic pulses from the applicator 1; 15. The resulting ultrasonic echo signals subsequently received by the applicator 1; 15 are amplified as electrical signals in a receiving amplifier 19, and are fed to an intensity modulating device 20 (Z amplifier) of a cathode ray tube 21. Image synthesis takes place in the form of a raster corresponding to an ultrasonic scanning raster as a function of horizontal time base pulses produced by a horizontal time base generator 22 and vertical time base pulses produced by a vertical time base generator 23. Both time base generators 22 and 23 are controlled by means of the sync pulses produced by the guide sync pulse generator 18.

A circuit arrangement for producing intensity modulating pulses for the guide beam 11 is denoted in FIG. 3 by the reference numeral 24. This circuit arrangement 24 comprises, in the first instance, a calculator 25 which determines the time (and hence the location on the image) at which an intensity modulating pulse for the guide beam 11 is to be produced as a function of the course of the time t of the horizontal time base pulses produced by the horizontal time base generator 22, and of course of time X of the vertical time base pulses produced by the vertical time base generator 23, and also as a function of the angle $\theta$, according to the following relationship:

$$t(X) = X/v \cdot \tan \theta,$$

where: $X = k + x$, and where: x is the sectional image coordinate (see FIG. 1); k again is the distance of the point of impact of the cannula 6 on the reference plane 12 for the guide beam 11 from the coordinate origin of the sectional image; and v is the sweep speed of the ultrasonic waves in the examination subject 2.

In order that the guide beam 11 is visible in the image from the point of impact of the cannula 6 on the reference plane 12, the vertical time base X does not commence at the left image edge (where $x = 0$) of the sectional image, but at the location $x = -k$, the emitting and counting circuit for the applicator 1; 15 being started only after sweeping of this distance k. This is achieved by means of a switch and a comparator in the transmitter control circuit (to be described in greater detail below), the switch being closed by the comparator when $X > k$.

When a fixed angle $\theta$ is prescribed, the angle $\theta$ can be programmed into the calculator 25 in advance by an angle adjusting device 26. However, if the angle $\theta$ is to be adjustable as a function of the position of the guiding aid 5 of the cannula 6, then control of the angle adjusting device 26 by position signals produced by an angle detecting element 27 (comprising a potentiometer) on the guide sleeve 8 according to the angle of the guide sleeve 8 firstly takes place, and adjustment of the calculator 25 to the given angle takes place subsequently by signals produced by the angle adjusting device 26.

Superimposing the bright points of the guide beam 11 onto the echo display image on the display screen of the cathode ray tube 21 can take place line by line, thereby producing a guide beam 11 having bright points following on in close succession. However, as already mentioned above, the guide beam 11 can also be superimposed as a measurement scale. A switch 29 in conjunction with an AND gate 28 and also with a further calculator 30 serves to switch over between the two possibilities. In the switching position of the switch 29 shown in FIG. 3, a potential H is always supplied to the switched input of the AND gate 28. Short output pulses of the calculator 25, occurring at the line sync frequency, arrive at the intensity modulating device 20 via the AND gate 28; this then produces bright points for the guide beam 11 which follow on in close succession at the line sync frequency.

When the switch 29 is switched over into the switching position indicated by a broken line in FIG. 3, relatively long output pulses produced by the calculator 30 are fed to the switched input of the AND gate 28. These output pulses are produced at time intervals:

$$\tau = a \cdot \cos \theta / v,$$

where a indicates the desired distance increment of the measurement scale, for example 5 mm; $\theta$ is again the target angle; and v is the speed of the ultrasonic waves in the examination subject 2. The pulses thus fed to the AND gate 28 only ever correspond to the line pulses of the calculator 25 with respect to time at fixed time intervals $\tau$, which are converted on the display screen into path distances between the individual bright points of the guide beam 11, as prescribed by a. Therefore, if, for example, a is selected to be 5 mm, then the guide beam 11 on the display screen of the cathode ray tube 21 is composed of bright points located along the guide beam 11 at distances of $a = 5$ mm. Therefore, the guide beam 11 corresponds to a superimposed, electronic measurement scale having 5 mm increments. This method presupposes an image having vertical line spacing, as is produced, for example, by line multiplication by digital television standards conversion. The length of pulses supplied by the calculator 30 should be at least equal to one horizontal time base period. In the whole superimposing process, superimposing takes place in such a way that the guide beam 11 is made visible on the left-hand side of the display screen before the actual echo sectional image begins with the cannula piercing point on the reference plane 12. As already mentioned above, the distance k of this piercing point from the coordinate origin of the sectional image is taken into account by using a comparator 31 in conjunction with a switch 32 for controlling the high frequency pulse generator 17. The switch 32 is only ever closed by the comparator 31 when the vertical time base voltage X reaches or exceeds a signal threshold k.

As an addition to, or even as an alternative to, the guide beam 11 (i.e. by momentarily switching the guide beam 11 off) a measuring image in the form of a cross can be superimposed on the echo display screen by means of an arrangement as described, for measuring distance and for measuring the puncture depth. For example, this is described in German Patent Application Nos. DE-PA 29 10 012.7, DE-PA 29 10 022.9 and DE-PA 29 09 999.8. For this, in the "biopsy" mode of operation, on the guide beam 11 or at that point which is prescribed by position and direction of the superimposed guide beam 11, a measuring mark simply needs to be guided to the target area 7 and the distance along the guide beam 11 to the reference plane 12 on the surface of the body measured by means of the distance measuring device and digitally indicated. The second measuring mark is then automatically fixed on the piercing point on the reference plane 12.

SUMMARY DISCUSSION

In a special development of the invention, the guidance aid 5 for the puncturing cannula 6 at the ultrasonic applicator 1 can contain an angle detector 27, FIG. 3, which as a function of the target angle θ respectively set, adjusts the guidance beam (indicated for diagrammatic convenience at 11 in FIGS. 1 and 2) in the visual image of the visual display to the target angle direction set, said adjustment being carried out with a corresponding positioning signal. Even simpler is an embodiment in which both the puncture angle θ at the guidance aid 5 as well as the target angle of the guidance beam in the ultrasonic visual image are set to a common, constant angle, whereby the targeting in the object by means of the guidance beam then ensues by means of shifting the ultrasonic applicator. Given today's very lightweight ultrasonic applicators, particularly such as are also constructed in the form of an ultrasonic array, thus, a targeting is possible without any additional preadjustment or postadjustment simply by means of shifting the applicator 1 without a particular exertion of force and with the required delicacy.

A mixing of lines into the echo visual image is likewise already known per se (for example, German OS 2,619,723), however, only in conjunction with distance measurements between two measuring marks, but not as a guidance line in conjunction with target aids for puncturing cannula.

Since the generation and mixing-in of the guidance beam must occur in coordination with the actual puncture direction of the puncturing cannula in the direction of the object to be punctuated, it is to be recommended, in a further advantageous development of the invention, to provide a calculator circuit 25 in the ultrasonic echo tomographic image device in the circuit arrangement for generating and mixing the guidance beam in, said calculator circuit continuously generating trace unblanking signals in the relevant segment of the image field as a function of the line clock signals of a horizontal time base generator 22 of the visual display, as well as controlled by the sweep signal of the vertical time base generator 23 of the same visual display as well as by an angle signal for the angular direction of the puncture, said trace unblanking signals combining in chronological succession to form the guidance beam. Thereby, if desired, the gating along the guidance beam can be selected by means of a special selection element 28-30 for the trace unblanking pulses at such points in time that unblanking points for the guidance beam always derive only at specific intervals from one another (for example, at 5 mm intervals). The guidance beam then exhibits the form of an electronic scale at which the depth of the object to be punctuated from the surface on which the applicator is resting can be immediately read without difficulties. The puncture path and the terminal point of the puncture path of the puncturing cannula can then also be continuously monitored and determined in the simplest manner in combination with a displaceable cursor as is likewise already known, for example, from the German LP 2,148,700 for Doppler measurements.

It will be apparent that many modifications and variations may be effected without departing from the scope of the novel concepts and teachings of the present invention.

I claim as my invention:

1. An ultrasound imaging apparatus for use with a puncturing device to facilitate puncturing of a body by said puncturing device, comprising (a) ultrasound signal applicator means adapted to be placed on said body for scanning a tissue region of said body, (b) imaging means responsive to output signals from said ultrasound signal applicator means for producing an image representative of said tissue region of said body, (c) guiding means coupled to said ultrasound signal applicator means for attaching a puncturing device thereto, (d) angle detecting means coupled to said guiding means for detecting the angle of a portion of said guiding means relative to said tissue region when said ultrasound signal applicator means is operationally coupled to said tissue region for scanning thereof, whereby the angle of a puncturing device relative to said tissue region may be determined when said puncturing device is attached to said guiding means for treatment of said body, and (e) directing circuit means coupled to said angle detecting means and responsive thereto for producing and superimposing on said body image a guide image beam having an orientation relative to said body image representative of the angle of said guiding means relative to said tissue region, whereby a desired orientation of said guiding means portion may be chosen to facilitate operation of a puncturing device attached thereto.

2. An ultrasound imaging apparatus according to claim 1, with said imaging means having an image signal means for coupling with said ultrasound signal applicator means, said directing circuit means comprising a guide beam circuit having input means coupled with said angle detecting means, said guide beam circuit being synchronized with said imaging means and controlled by said input means for producing an intensity modulating signal, and having output means coupled with said image signal means for superimposing the intensity modulating signal on the output signals from the ultrasound signal applicator means so as to superimpose said guide image beam on said body image.

3. An apparatus according to claim 2, wherein the directing circuit means is adapted such that, in use, the guide image beam is maintained at a fixed position with respect to the body image, corresponding to a fixed position of the guiding means and hence the puncturing device with respect to said applicator means, puncturing of the body in substantially the desired direction being achieved by displacement of the applicator means with respect to the body.

4. An apparatus according to claim 3, wherein the directing circuit means comprises a calculator for producing an intensity modulating signal for supply to said imaging means for producing the guide image beam.

5. An apparatus according to claim 4, wherein the intensity modulating signal is produced in use as a function of a horizontal time base signal and a vertical time base signal from said imaging means and as a function of a signal from the angle detecting means.

6. Apparatus according to claim 5, wherein the intensity modulating signal is produced in use according to the relationship:

$$t(X) = X/v \cdot \tan \theta;$$

where: $X = x + k$; and where: t is the course of horizontal time base pulses of the horizontal time base signal; X is the course of vertical time base pulses of the vertical time base signal; v is the sweep speed of ultrasonic waves in the body being treated; $\theta$ is an angle detected by the angle detecting means; x is an image coordinate of a target area of the body to be punctured by such a puncturing device; and k is the distance from a point of intersection of the puncturing device with a reference plane for the guide image beam from the image coordinate origin.

7. Apparatus according to claim 6, further comprising means for superimposing, on an image of a body displayed by said imaging means, a measuring image which can be displaced, with respect to the body image, to a target area in the body image, and means for measuring the displacement of the measuring image from a reference point on the surface of the body to the target area.

8. Apparatus according to claim 7, wherein the the reference point is located on the said reference plane.

9. Apparatus according to claim 4, wherein the intensity modulating signal comprises a series of pulses.

10. Apparatus according to claim 2, further comprising means for superimposing, on an image of a body displayed by said imaging means, a measuring image which can be displaced, with respect to the body image, to a target area in the body image, and means for measuring the displacement of the measuring image from the reference point on the surface of the body to the target area.

11. Apparatus according to claim 2 with said guiding means having a puncturing device guided thereby comprising a cannula.

12. Apparatus according to claim 1, wherein the imaging means produces the body image as a series of lines, and the directing circuit means comprises a calculator for producing an intensity modulating signal, said directing circuit means being operable during generation of successive lines of the body image for coupling said intensity modulating signal with said imaging means to superimpose said guide image beam on said body image.

13. Apparatus according to claim 12, wherein the imaging means generates a horizontal time base signal controlling the producing of the series of lines of the body image, and generates a vertical time base signal coordinated with the scanning of said applicator means, the intensity modulating signal being produced in use as a function of the horizontal time base signal from said imaging means, and as a function of a signal from the angle detecting means.

14. Apparatus according to claim 12, wherein the intensity modulating signal comprises a series of intensity modulating pulses.

15. Apparatus according to claim 14, wherein the series of intensity modulating pulses produce the guide image beam by producing a corresponding series of intensity modulated spots on an image displayed by said imaging means in use.

16. Apparatus according to claim 15, wherein the imaging means produces the body image as a series of lines with line synchronization pulses, and the intensity modulating pulses are produced in timed relation to the line synchronization pulses.

17. Apparatus according to claim 15, wherein the intensity modulating pulses are produced at regular intervals such that the intensity modulated spots are produced at regular intervals along the guide image beam and such that the guide image beam is in the form of a scale.

18. Apparatus according to claim 14, wherein the intensity modulating signal is produced in use according to the relationship:

$$t(X) = X/v \cdot \tan \theta;$$

where: $X = x + k$; and where: t is the course of horizontal time base pulses of the horizontal time base signal; X is the course of vertical time base pulses of the vertical time base signal; v is the sweep speed of ultrasonic waves in the body being treated; $\theta$ is an angle detected by the angle detecting means; x is an image coordinate of a target area of the body to be punctured by such a puncturing device; and k is the distance from a point of intersection of the puncturing device with a reference plane for the guide image beam from the image coordinate origin.

19. Apparatus according to claim 18, provided with a second calculator, associated with the first-mentioned calculator, for producing output pulses at time intervals $\tau$, where:

$$\tau = a \cdot \cos \theta / v;$$

where a is a predetermined increment for the scale.

20. Apparatus according to claim 19, wherein the predetermined increment is approximately 5 mm.

21. Apparatus according to claim 19, the imaging means having intensity modulating circuitry, and an AND gate having first and second inputs which are connectable with outputs of the first-mentioned and second calculators respectively such that, in use, in order to produce a guide image beam in the form of a scale, pulses are supplied by an output of the AND gate to said intensity modulating circuitry of said imaging means only when an intensity modulating signal produced by the first-mentioned calculator coincides with an output pulse from the second calculator.

22. Apparatus according to claim 1, further comprising means for superimposing, on an image of a body displayed by imaging means, a measuring image which can be displaced, with respect to the body image, to a target area in the body image, and means for measuring the displacement of the measuring image from a reference point on the surface of the body to the target area.

23. Apparatus according to claim 22, wherein the measuring image is displaced, in use, along the guide image beam.

24. Apparatus according to claim 22, provided with means for digitally indicating the measured displacement of the measuring image.

25. Apparatus according to claim 22, provided with means for automatically superimposing, on the body image at the said reference point, a further measuring image for indicating the point on the body surface at which the puncturing device should enter the body.

26. Apparatus according to claim 1 with a puncturing device guided by said guiding means.

27. Apparatus according to claim 26 with said puncturing device being angularly adjustable jointly with the portion of said guiding means which is coupled with said angle detecting means.

28. Apparatus according to claim 26, wherein the puncturing device comprises a cannula.

29. Apparatus according to claim 28, wherein the guiding means comprises a guide sleeve for a needle associated with the cannula, the guide sleeve being detachably mounted on the guiding means such that, in use, after puncturing of a body, the applicator means can be detached from the cannula and removed.

* * * * *